United States Patent [19]

Baldi et al.

[11] 4,182,874

[45] Jan. 8, 1980

[54] PROCESS FOR THE PRODUCTION OF CHLORO-BIS(ALKYLAMINO)-S-TRIAZINES

[75] Inventors: Luciano Baldi, Turin; Giuliano Giorcelli, Borgaro T.se Turin; Renato Francese, Turin, all of Italy

[73] Assignee: Rumianca S.p.A., Turin, Italy

[21] Appl. No.: 953,320

[22] Filed: Oct. 20, 1978

[30] Foreign Application Priority Data

Oct. 20, 1977 [IT] Italy ............................. 28808 A/77

[51] Int. Cl.$^2$ ......................................... C07D 251/50
[52] U.S. Cl. .................................................. 544/204
[58] Field of Search ....................................... 544/204

[56] References Cited

U.S. PATENT DOCUMENTS 3,681,337  8/1972  Petree ................................... 544/204

Primary Examiner—John M. Ford
Attorney, Agent, or Firm—Sughrue, Rothwell, Mion, Zinn and Macpeak

[57] ABSTRACT

The commercial method of preparing chloro-bis(alkylamino)-s-triazine by step-wise replacement of two chlorine atoms of cyanuric chloride by means of alkylamino groups in an alkaline medium comprising water and a liquid organic compound is improved by adding to the reaction product, upon completion of the second replacement step, or during or after the distillation of the organic compound, at least 0.5% by weight with respect to the weight of the chloro-bis(alkylamino)-s-triazine, of minerals chosen from the groups of montmorillonite, paligorskite, vermiculite and chlorite and having a base-exchange capacity of at least 10 milli-equivalents for each 100 grams of said solid, thus deactivating the unreacted alkylamine and the tris(alkylamino)-s-triazines present in the reaction product.

9 Claims, No Drawings

PROCESS FOR THE PRODUCTION OF CHLORO-BIS(ALKYLAMINO)-S-TRIAZINES

The present invention relates to an improved procedure for the preparation of chloro-bis(alkylamino)-s-triazines having high characteristics of handling and formulability.

The chloro-bis(alkylamino)-s-triazines are compounds definable by means of the general formula:

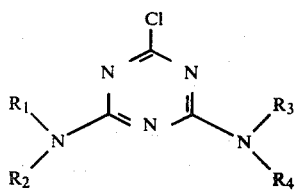

where $R_1$, $R_2$, $R_3$ and $R_4$ independently are hydrogen, an alkyl radical containing from 1 to 5 atoms of carbon, or particular groups of a different nature from the alkyl group.

The chloro-bis(alkylamino)-s-triazines are valued herbicides and the compounds most known belonging to this group are: 2-chloro-4-ethylamino-6-isopropylamino-s-triazine (atrazine), 2-chloro-4,6-bis(ethylamino)-s-triazine (simazine) and 2-chloro-4,6-bis-(isopropylamino)-s-triazine (propazine). The herbicidal characteristics of these compounds are described in U.S. Pat. No. 2,891,855 here given as a reference.

The chloro-bis(alkylamino))-s-triazines are generally prepared from cyanuric chloride by step-wise replacement of two atoms of chlorine, as reported, for example, by W. Pearlman and C. K. Banks in J. Am. Chem. Soc. 70, 3726 (1948). In practice the reaction is carried out according to the general scheme:

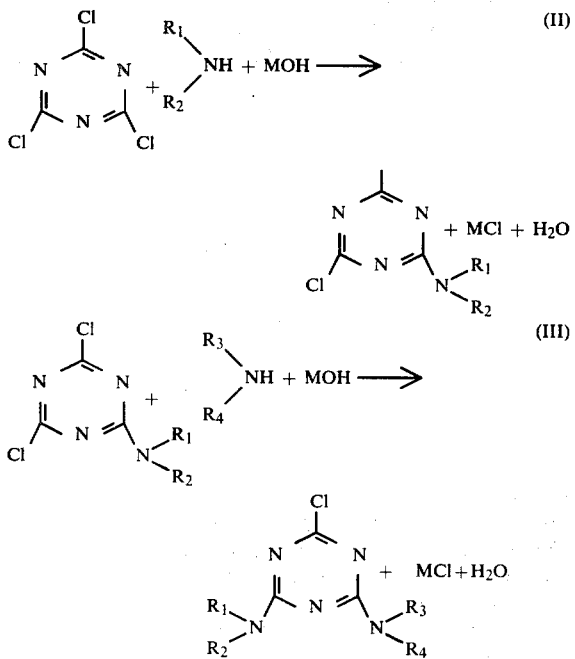

where M represents an alkali metal.

In particular the preparation of atrazine is generally carried out by a discontinuous method, by reacting, in a first reaction stage, cyanuric chloride with isopropylamine in the presence of sodium hydroxide to give 2,4-dichloro-6-isopropylamino-s-triazine. This latter is reacted, in a second stage, with ethylamine and with a further quantity of sodium hydroxide with the subsequent formation of the desired product: 2-chloro-4-ethylamino-6-isopropylamino-s-triazine.

The reactions described may be carried out in an aqueous medium or in an organic medium. Generally it is preferred to conduct the reactions in a water-organic compound medium, using as organic compound a solvent for cyanuric chloride which is insoluble in water, or is partially or totally soluble in the same, and thus two-phase or single-phase water-organic compound systems.

Generally the reaction (II) given above is carried out by using stoichiometric quantities of the reagents, while the reaction (III) is carried out with a quantity of alkylamine and of sodium hydroxide greater than those needed for the production of chloro-bis(alkylamino)-s-triazine. This method of operation is justified by the need to completely convert the 2,4-dichloro-6-alkylamino-s-triazine in view of the undesirable characteristics of such compounds. Thus, for example, 2,4-dichloro-6-isopropylamino-s-triazine has skin-irritant properties to such an extent that it must not be present in the final product in quantities greater than about 0.5% by weight.

On the other hand the use of excess alkylamine results in disadvantages due to the formation of tris(alkylamino)-s-triazine, by reaction of the excess alkylamine with the chloro-bis (alkylamino)-s-triazine. For example, the reaction of ethylamine with 2-chloro-4-ethylamino-6-isopropylamino-s-triazine results in the formation of 2,4-bis(ethylamino)-6-isopropylamino-s-triazine. This latter compound is undesirable in that it renders the recovery of atrazine from the reaction products difficult, hinders the grinding of the dried atrazine and reduces the stability and flowability of the liquid formulations containing atrazine. Probably these undesirable effects are caused, at least in part, by the 2,4-bis-(ethylamino)-6-isopropylamino-s-triazine, which is a tacky solid of low melting point and waxy appearance. This by-product mainly forms in the stage of recovery of the reaction products, especially in the stage of distillation of the organic solvent used in the reaction medium, rather than during the reaction (III) described above.

Therefore various expedients have been proposed in the art to separate, or at least to render to some extent non-active, the unreacted alkylamine at the end of the reaction (III) and in particular to separate, or to deactivate, the ethylamine in the case of the preparation of atrazine.

Thus, for example, according to U.S. Pat. No. 3,681,335 on completion of the formation of the chloro-bis(alkylamino)-s-triazine, a strong acid is added to the reaction medium to bring the pH from 11.5–12 to values of the order of 5–9 (preferably of the order of 6.5–7.5). In this manner the alkylamine is deactivated and the distillation of the organic solvent may be carried out without danger of formation of tris(alkylamino)-s-triazine. According to the patent under discussion, the pH is brough back to values of the order of 11–12.5 in the residual suspension from the distillation containing the chloro-bis(alkylamino)-s-triazine before the separation of the latter is carried out by means of filtration. The characteristics of filterability are thus improved.

Moreover, according to U.S. Pat. No. 3,681,337, immediately after the end of reaction (III), cyanuric chloride is added to the reaction mixture in such amounts as to neutralize the free amine and form the dichloro-alkylamino-s-triazine, which is then hydrolized together with the free cyanuric chloride. Since the hydrolysis products are soluble in water their removal becomes easy.

Finally, according to U.S. Pat. No. 3,705,156 formaldehyde is added to the products of the reaction (III), in order to induce the formation of condensation products between formaldehyde and the free alkylamine. These condensation products are removed during the distillation and the subsequent filtration.

These known processes only achieve the object of minimising the formation of the tris(alkylamino)-s-triazine and also have disadvantages resulting from the conversion of the excess alkylamine into new chemical species which must be removed from the reaction product.

It is an object of the present invention to provide a method for rapid deactivation of the unreacted alkylamine and the tris(alkylamino)-s-triazine present in the reaction products by means of substances which do not affect the properties of the desired product and which do not require any separation from the latter. It is a further object of the present invention to provide a process for preparing chloro-bis(alkylamino)-s-triazines which have high characteristics of formulability.

More particularly, the present invention provides a process for preparing chloro-bis(alkylamino)-s-triazine by step-wise replacement of two chlorine atoms of cyanuric chloride by means of alkylamino groups in an alkaline medium comprising water and a liquid organic compound which is a solvent for cyanuric chloride, in which a molar excess of alkylamine is used in the second replacement step and in which said organic compound is removed by distillation from the reaction mixture resulting from the second replacement step, characterized by adding to said reaction mixture, upon completion of the second replacement step, or during or after the distillation of the organic compound, at least 0.5% by weight with respect to the weight of the chloro-bis-(alkylamino)-s-triazine, of one or more inorganic solids, said solids being selected from minerals belonging to the groups of montmorillonite, paligorskite, vermiculite and chlorite and having a base-exchange capacity of at least 10 milli-equivalents for each 100 grams of said solid.

The molar excess of alkylamine used in the substitution of the second chlorine atom of cyanuric chloride generally does not exceed 15% and is preferably from 1 to 5%, best results being generally obtained with values of about 3%. With this excess it is in fact possible to convert completely, or substantially completely, the 2,4-dichloro-6-alkylamino-s-triazine.

As has been said the exchange solid is used in an amount of at least 0.5% by weight with respect to the weight of the chloro-bis(alkylamino)-s-triazine. The maximum amount of the solid is not particularly critical and depends on the excess of alkylamine used in the substitution of the second chlorine atom of cynauric chloride. It has been found that it is not generally necessary to exceed about 3% by weight of exchange solid with respect to the weight of the chloro-di(alkylamino)-s-triazine to obtain the desired effects. It is thought that the exchange solid acts is various ways according to the moment at which it is added, that is either by blocking the free alkylamine or the tri-substituted derivative which, among the triazine derivatives present in the reaction medium, is the most basic. Whatever the explanation, the fact remains that by means of the process of the present invention it is possible to obtain chloro-bis-(alkylamino)-s-triazines characterised by extremely high characteristics of formulability.

Moreover, since the said exchange solid remains as an inert filler in the chloro-di(alkylamino)-s-triazine and does not have a detrimental effect on the characteristics of the formulations, the process of the present invention is simple and convenient.

The chloro-bis(alkylamino)-s-triazines obtained according to the present invention are useful in herbicidal formulations (both as wettable powders and as liquid suspensions) which are characterised by a great facility of use and by an increased herbicidal efficiency. These formulations do not have any of those known disadvantages resulting from the presence of tris(alkylamino)-s-triazines in their storage or their use.

By means of the process of the present invention there may be prepared all the compounds definable by means of the general formula (I), in which $R_1$, $R_2$, $R_3$ and $R_4$ independently are hydrogen, alkyl radicals either the same of different, having from 1 to 5 atoms of carbon, or other particular groups different from alkyl groups. Examples of alkyl radicals are: methyl, ethyl, isopropyl, cyclopropyl, n-butyl, sec-butyl and tert-butyl.

In the description which follows, specific reference will be made to the preparation of 2-chloro-4-ethylamino-6-isopropylamino-s-triazine. This is for reasons of simplicity, it being taken into account that wholly similar considerations are valid for the other chloro-di(alkylamino)-s-triazines.

(a) Preparation of 2,4-dichloro-6-isopropylamino-s-triazine

In stage (a) cyanuric chloride, isopropylamine and sodium hydroxide are reacted to produce 2,4-dichloro-6-isopropylamino-s-triazine according to the following scheme:

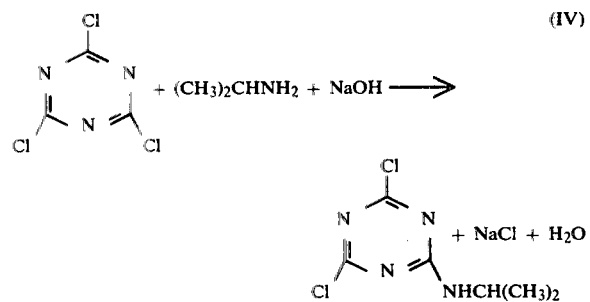

The quantities of isopropylamine and of sodium hydroxide are equivalent, or nearly equivalent, to those needed for the formation of the 2,4-dichloro-6-isopropylamino-s-triazine. In place of sodium hydroxide there may be used sodium carbonate, or the hydroxide or carbonate of other alkali metals, such as lithium and potassium.

The reaction is carried out in the presence of an organic compound, inert under the reaction conditions and having a good solvating power towards cyanuric chloride. Organic solvents suitable for the purpose are: diethyl ether, dioxan, diethyl Cellosolve, benzene, toluene, xylene, chlorobenzene, acetone, methyl ethyl ketone, carbon tetrachloride or such other organic solvents known in the art in respect of the preparation of chloro-bis(alkylamino)-s-triazines. There solvents are preferably used in mixture with water, in the form of a single-phase system, such as water-acetone and water-dioxan, or a two-phase system, such as water-benzene and water-chlorobenzene. As a rule the cyanuric chloride is fed in in the form of a solution in the chosen organic solvent, while the inorganic base and the alkylamine are fed in in the form of an aqueous solution. In the choice of the solvent it is also necessary to take account of its separability, by means of distillation, from the 2-chloro-4-ethylamino-6-isopropylamino-s-triazine finally produced. The quantities of organic solvent and of water used are not particularly critical; it is however, convenient to maintain the weight ratios between the two at values of from 3:1 to 3:2. Moreover good results are obtained by regulating the feeds such that the concentration of the 2,4-dichloro-6-isopropylamino-s-triazine at the end of stage (a) is from 10 to 20% by weight with respect to the weight of the chosen organic solvent.

The temperature is generally kept at a value of from −5° to 60° C. Overpressure is not generally applied, or the overpressure necessary to maintain the reaction medium in the liquid phase is applied.

The 2,4-dichloro-6-isopropylamino-s-triazine may be prepared by using a continuous or a discontinuous process. In the second case the sodium hydroxide and the isopropylamine are generally added in the form of aqueous solutions to the cyanuric chloride dissolved in the chosen organic solvent.

At the end of stage (a) it is possible to carry out a separation of materials from the reaction mixture, such as the aqueous phase, or the reaction mixture may be conveyed directly to the following reaction stage.

(b) Preparation of
2-chloro-4-ethylamino-6-isopropylamino-s-triazine

In stage (b) the 2,4-dichloro-6-isopropylamino-s-triazine obtained in stage (a), ethylamine and sodium hydroxide, are reacted to produce 2-chloro-4-ethylamino-6-isopropylamino-s-triazine according to the scheme:

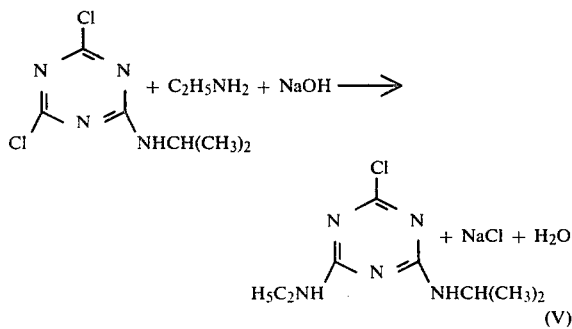

The ethylamine and sodium hydroxide are generally used in a molar excess of from 1% to 5%. Usually this excess is maintained at values of the order of 3%. The ethylamine and the sodium hydroxide are conveniently fed in in the form of an aqueous solution.

The reaction is conveniently carried out at a temperature of from 25° to 90° C. and for a period such as to completely convert the 2,4-dichloro-6-isopropylamino-s-triazine, or at least to convert more than 99.5% of this compound.

The other operating conditions for stage (b) are entirely similar to those described for stage (a).

(c) Neutralisation of the ethylamine and separation of the products from the reaction To the reaction mixture coming from stage (b) is added an exchange solid suitable for neutralising the free ethylamine. This addition may be carried out within 5–10 minutes from the end of stage (b) and before the distillation of the organic solvent.

For this purpose there may be used porous exchange solids of mineral origin, belonging to the general group of clays generally defined as sediments of natural origin (including those obtained by alteration "in situ" under the action of supergene and under the action of hydrothermic processes) or as sedimentary rocks composed of one or more minerals and additional compounds, the whole usually being rich in hydrated silicates of aluminium, iron and magnesium, hydrated alumina, or iron oxide, with particles predominantly in the colloidal or nearly colloidal range and which generally develop plasticity if sufficiently pulverised or humidified. In particular the solids useful for the purposes of the present invention consist of minerals of the groups of montmorillonite, of paligorskite, of vermiculite and of chlorite. In the montmorillonite group are included the minerals: montmorillonite, beidellite, montronite, hectorite, saponite, and sauconite. These minerals have a high base-exchange capacity (cationic), in general of the order of 80–90 milli-equivalents or more for each 100 g of mineral dried in air. The said minerals, suitably dried and ground, form viscous, thixotropic suspensions with water and may exchange inorganic and organic cations and anions, as well as forming complexes by interaction with organic polar molecules, without phenomena of ionic exchange. Bentonites, consisting of minerals of the montmorillonite type, as well as other minerals of the clay group and variable quantities of non-argillaceous minerals, are also useful for the purposes of the present invention, as well as the mineral attapulgite (included in the paligorskite group) which has a base exchange capacity of the order of 20 milliequivalents for each 100 g of dry mineral.

For further information relating to the solids in question, we refer to the following literature which is given here as a reference: Kirk-Othmer "Encyclopedia of Chemical Technology", (1964), Volume 3, pages 339–360 and Volume 5, pages 541–581.

In one embodiment the exchange solid is added to the reaction mixture discharged from stage (b) in powder form, for example in the form of granules with a size of 20–250 microns and its action of neutralising the ethylamine is rapid. It is in fact sufficient to maintain agitation for a few minutes (1–2 minutes). The operating temperature is not particularly critical. Thus the solid may be added at the temperature at which the reaction mixture is discharged from stage (b), it also being possible to operate within a wider range such as from 40° to 100° C.

The distillation of the organic solvent is then carried out, by operating at a pressure equal to or less than atmospheric. The distillation residue generally consists of a dense suspension of the 2-chloro-4-ethylamino-6-isopropylamino-s-triazine and also contains the base-exchange solid. This suspension is filtered and finally the recovery of the atrazine is carried out according to the known art.

According to a further embodiment, the exchange solid is added to the reaction mixture, still in powder form, during or preferably after the distillation of the organic solvent and its blocking action towards the tris(alkylamino) triazine derivatives is in every case rapid. In the case of addition at the end of the distillation it is sufficient to maintain the resulting mass under agitation for a brief period (in general of the order of 10–15 minutes) and the operating temperature is not particularly critical. Thus it is possible to add the solid at the temperature which the reaction mixture reaches at the end of the distillation of the organic solvent, it also being possible to operate within a wider range of values such as from 60° to 110° C.

The filtration of the suspension is finally started and finally recovery of the atrazine is carried out according to the known art. Both the embodiments of the present invention result in the obtaining of atrazine having optimal characteristics of formulability.

The small quantity of porous solid in the atriazine may be considered as an inert substance in the final formulation, which does not impede the formulability, and even favours it.

This filler does not alter the biological efficiency of the active principle, atrazine, as a herbicide in the least, nor does it alter the level of toxicity of the said product. Additives similar to the filler under discussion are for the rest classified as free from the need for tolerance according to the United States norms given in the "Code of Federal Regulations" 40, Protection of environment 180, 1001 (C) and (E), (reviewed the 1st June 1975) where the solids in question are classified as solid and inert diluents.

Moreover the fact that the improvement of the formulability is linked to the particular characteristics of the materials under discussion is shown by the fact that tests carried out with other types of inorganic solids, for example acidic alumina, adsorbent carbon and Celite, have not produced such desirable results.

EXAMPLE 1

A reactor of 20 liter capacity, provided with an agitator, a thermometer and two separate apertures for the feed of the reagents, is used. The reactor is furnished with means for its cooling. Into the reactor are loaded initially a solution of about 1840 g (10 moles) of cyanuric chloride in about 5000 g of toluene (boiling point 110.6° C.). Hardly has the temperature of the solution stabilised at 5° C. than there are simultaneously added, under strong agitation, 840 g of an aqueous solution containing 70% by weight of isopropylamine (10 moles) and 1340 g of an aqueous solution containing 30% by weight of sodium hydroxide (10 moles). The two feed rates are controlled so that the addition of the isopropylamine solution finishes in 25 minutes and that of the sodium hydroxide in 28 minutes.

During the addition, the temperature rises from 5° C. up to 20°–22° C., while the pH, from an initial value of 2–3, rises to a maximum value of 9.5 then to fall to 6–7.

After the addition, the mixture is maintained for 10 minutes at 20° C., 2000 g of dilute hydrochloric acid (0.1% by weight) are introduced so as to bring the pH of the medium to a value of about 2–3. The mixture is agitated for 15 minutes and then decanted and the aqueous layer is separated.

To the solution of 2,4-dichloro-6-isopropylamino-s-triazine in toluene remaining in the reactor are added, under strong agitation, about 915 g of an aqueous solution containing 50% by weight of ethylamine (10.15 moles) and about 1353 g of an aqueous solution containing 30% by weight of sodium hydroxide (10.15 moles). The said solutions are added in the same manner as in the first reaction step. During the second addition the temperature rises from 25° to 50° C. and the final pH is equal to 11.–12. The dense suspension thus obtained is divided into two parts as quickly as possible. One part (A) is submitted to distillation to remove the toluene in the form of an azeotropic toluene-water mixture, by operating at 85°–100° C. To the distillation residue are added 3,700 ml of water and the suspension thus obtained is filtered at 60° C. The filtered solid is washed until the sodium chloride has been removed completely. After drying for ten hours in an oven at 100° C., 2-chloro-4-ethylamino-6-isopropylamino-s-triazine is obtained with a yield of the orde of 96%.

The other part (B) is admixed with bentonite, consisting essentially of montmorillonite, having the following characteristics:

grain size: from 20 to 250 microns
apparent density: 1 g/cm$^3$
base-exchange capacity: 100 m.eq./100 g.

The quantity of bentonite added is given in Table I as a percentage by weight with respect to the weight of the 2-chloro-4-ethylamino-6-isopropylamino-s-triazine. The suspension thus obtained is maintained for 20 hours at 50° C. The sample (B) is then submitted to the treatments of distillation and recovery of atrazine from the distillation residue, by operating under the same conditions as in the case of sample (A).

The product obtained from sample (A) consists of atrazine with a purity of about 98%. The product obtained from sample (B) contains about 1% of bentonite and atrazine with a purity of the order of 98%.

Suspension are prepared from the products obtained from samples (A) and (B) with a concentration of 45% by dispersing the finely ground atrazine in a liquid medium consisting of water, wetting agents, dispersing agents and suspending agents. The fluidity of the formulate is determined immediately after the formulation and after one month and six months of storage under ambient conditions. The results are summarized in Table I.

EXAMPLES 2 AND 3

Two runs are carried out as in Example 1 using respectively 3% and 6% molar excess of ethylamine with respect to the stoichiometric value. The quantity of bentonite added is given in Table I as a percentage by weight with respect to the 2-chloro-4-ethylamino-6-isopropylamino-s-triazine.

The results are summarised in Table I. The content of 2,4-bis(ethylamino)-6-isopropylamino-s-triazine in the products obtained from the samples (B) is in every case less than the quantity which can be determined analytically.

EXAMPLE 4

The preparation of the atrazine is carried out as in Example 1 without subdividing the suspension which is obtained after substitution of the second atom of chlorine of the cyanuric chloride. This suspension is maintained for 20 hours at 50° C. and then subjected to distillation to recover the toluene in the form of an azeotropic toluene-water mixture, by operating at 85°–100° C.

The distillation residue is subdivided into two parts. One part (A) is filtered at 60° C. and the filtered solid is washed with water until the sodium chloride has been removed completely. After drying for 10 hours in an oven at 100° C., atrazine is obtained with a yield of about 96%.

The other part (B) is admixed with bentonite and is maintained for 10–15 minutes under agitation at 60°–100° C. The suspension is then filtered at 60° C. and the filtered solid is washed until the sodium chloride has been eliminated completely. After drying in an oven at 100° C. atrazine is obtained with a yield of about 96%. The quantity of bentonite used is given in Table I as a percentage by weight with respect to the 2-chloro-4-ethylamino-6-isopropylamino-s-triazine.

Suspension are prepared from the products obtained from samples (A) and (B) with a concentration of 45% by dispersing the finely ground atrazine in a liquid medium consisting of water, wetting agents, dispersing agents and suspending agents.

The fluidity of the formulate is determined immediately after the formulation and after one and six months of storage under ambient conditions. The results are summarized in Table I.

EXAMPLES 5 AND 6

Two runs are carried out as in Example 4 using respectively 3% and 6% molar excesses of ethylamine with respect to the stoichiometric value. The quantity of bentonite added is given in Table I as a percentage by weight with respect to the 2-chloro-4-ethylamino-6-isopropylamino-s-triazine. The results are summarized in Table I.

EXAMPLE 7

Three runs are carried out as in Example 1, using respectively in place of the bentonite the following substances:
acidic alumina
adsorbent carbon
Celite The suspensions with 45% concentration prepared from the products thus obtained are subjected to measurement of the fluidity immediately after formulation and during storage under ambient conditions.

In all the cases after 20 days of storage the suspensions had reached high values of the viscosity.

EXAMPLE 8

Three runs are carried out as in Example 4 using respectively in place of the bentonite the following compounds:
—acidic alumina
—adsorbent carbon
—Celite The results of the tests carried out on the formulations are wholly similar to those obtained in Example 7.

TABLE I

| Ex. | Sample | % molar excess Et NH$_2$ | % bentonite | initial | fluidity after one month | after 6 months |
|---|---|---|---|---|---|---|
| 1 | A | 1.5 | — | fluid | viscous | — |
| 1 | B | 1.5 | 1 | fluid | fluid | fluid |
| 2 | A | 3.0 | — | fluid | viscous | — |
| 2 | B | 3.0 | 2 | fluid | fluid | fluid |
| 3 | A | 6.0 | — | fluid | viscous | — |
| 3 | B | 6.0 | 3 | fluid | fluid | fluid |
| 4 | A | 1.5 | — | fluid | viscous | — |
| 4 | B | 1.5 | 1 | fluid | fluid | fluid |
| 5 | A | 3.0 | — | fluid | viscous | — |
| 5 | B | 3.0 | 2 | fluid | fluid | fluid |
| 6 | A | 6.0 | — | fluid | viscous | — |
| 6 | B | 6.0 | 3 | fluid | fluid | fluid |

We claim:

1. In a process for preparing chloro-bis(alkylamino)-s-triazine by step-wise replacement of two chlorine atoms of cyanuric chloride by means of alkylamino groups in an alkaline medium comprising water and a liquid organic compound which is a solvent for cyanuric chloride, in which a molar excess of alkylamine is used in the second replacement step and in which said organic compound is removed by distillation from the reaction mixture resulting from the second replacement step, the improvement which comprises adding to said reaction mixture, upon completion of the second replacement step, or during or after the distillation of the organic compound, at least 0.5% by weight with respect to the weight of the chloro-bis (alkylamino)-s-triazine, of one or more inorganic solids, said solids being selected from minerals belonging to the groups of montmorillonite, paligorskite, vermiculite and chlorite and having a base-exchange capacity of at least 10 milliequivalents for each 100 grams of said solid.

2. The process of claim 1, wherein said molar excess of alkylamine does not exceed 15%.

3. The process of claim 1, wherein said molar excess of alkylamine is from 1 to 5%.

4. The process of claim 1, wherein said inorganic solids are added in an amount of from 0.5 to 3% by weight with respect to the weight of chloro-bis(alkylamino)-s-triazine.

5. The process of claim 1, wherein said inorganic solids are added within a period of 10 minutes from the completion of the second replacement step.

6. The process of claim 1, wherein said inorganic solids are added in powder form to the reaction mixture resulting from the second replacement step, the resulting mass is stirred for a few minutes at a temperature of from 40° to 100° C. and the organic compound is then removed by distillation.

7. The process of claim 1, wherein said inorganic solids are added in powder from after distillation of the organic compound, the resulting mass being stirred for a period not exceeding about 15 minutes at a temperature of from 60° to 110° C.

8. The process of claim 1, wherein said minerals belong to the montmorillonite group.

9. The process of claim 1, wherein said inorganic solid is bentonite.

* * * * *